United States Patent [19]
Cloyd

[11] 3,972,330
[45] *Aug. 3, 1976

[54] SYRINGE

[75] Inventor: Harold S. Cloyd, Erie, Pa.

[73] Assignee: Nosco Plastics, Inc., Erie, Pa.

[ * ] Notice: The portion of the term of this patent subsequent to Oct. 23, 1990, has been disclaimed.

[22] Filed: Aug. 10, 1972

[21] Appl. No.: 279,504

Related U.S. Application Data

[60] Division of Ser. No. 98,226, Dec. 15, 1970, Pat. No. 3,766,919, and a continuation-in-part of Ser. No. 749,448, Aug. 1, 1968, abandoned.

[52] U.S. Cl. .......................... 128/220; 128/218 P
[51] Int. Cl.² .......................................... A61M 5/00
[58] Field of Search ............ 128/220, 218 P, 218 N, 128/221, 218 R, 215

[56] References Cited
UNITED STATES PATENTS

| | | | |
|---|---|---|---|
| 1,770,632 | 7/1930 | Smith | 128/220 |
| 1,848,711 | 3/1932 | Hall | 128/200 |
| 2,478,845 | 8/1949 | Smith | 128/220 |
| 2,551,414 | 5/1951 | Burnside | 128/218 N |
| 2,864,364 | 12/1958 | Mizzy | 128/220 |
| 3,098,482 | 7/1963 | O'Sullivan | 128/220 |
| 3,128,766 | 4/1964 | Mizzy | 128/220 |
| 3,376,866 | 4/1968 | Ogle | 128/272 X |

FOREIGN PATENTS OR APPLICATIONS

| | | | |
|---|---|---|---|
| 162,115 | 12/1953 | Australia | 128/220 |
| 85,146 | 3/1958 | Denmark | 128/218 N |
| 1,441,390 | 11/1968 | Germany | 128/220 |

*Primary Examiner*—John D. Yasko
*Attorney, Agent, or Firm*—Ralph Hammar

[57] ABSTRACT

An inverted type syringe for use with a vial having a stopper piston closing at one end of the vial. Complementary male and female connectors on the upper end of the hub and the adjacent portion of the piston establish a push or pull connection between the piston and the hub. As the connectors are engaged, the piston is punctured so pressure on the vial causes ejection of the contents.

4 Claims, 3 Drawing Figures

INVENTOR
Harold S Cloyd
BY
Ralph Hammar
ATTORNEY

SYRINGE

This is a division of application Ser. No. 98,226, filed Dec. 15, 1970 (incorporated by reference), now U.S. Pat. No. 3,766,919 and a continuation-in-part of application Ser. No. 749,448, filed Aug. 1, 1968 (incorporated by reference), now abandoned.

This invention is intended to simplify the molding of inverted type syringes so the cost can be made low enough for one-time use.

In the drawing, FIG. 1a, is a sectional view of the syringe as packed for shipment;

Figure 2A:
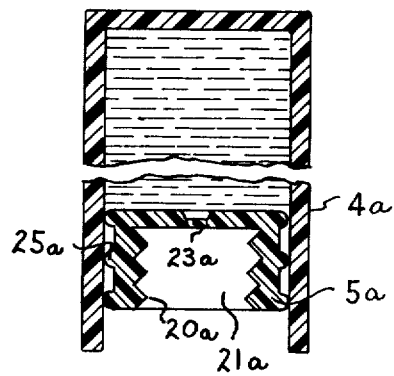
FIG. 2a, is a section through the vial for use with the syringe.
Figure 1A:
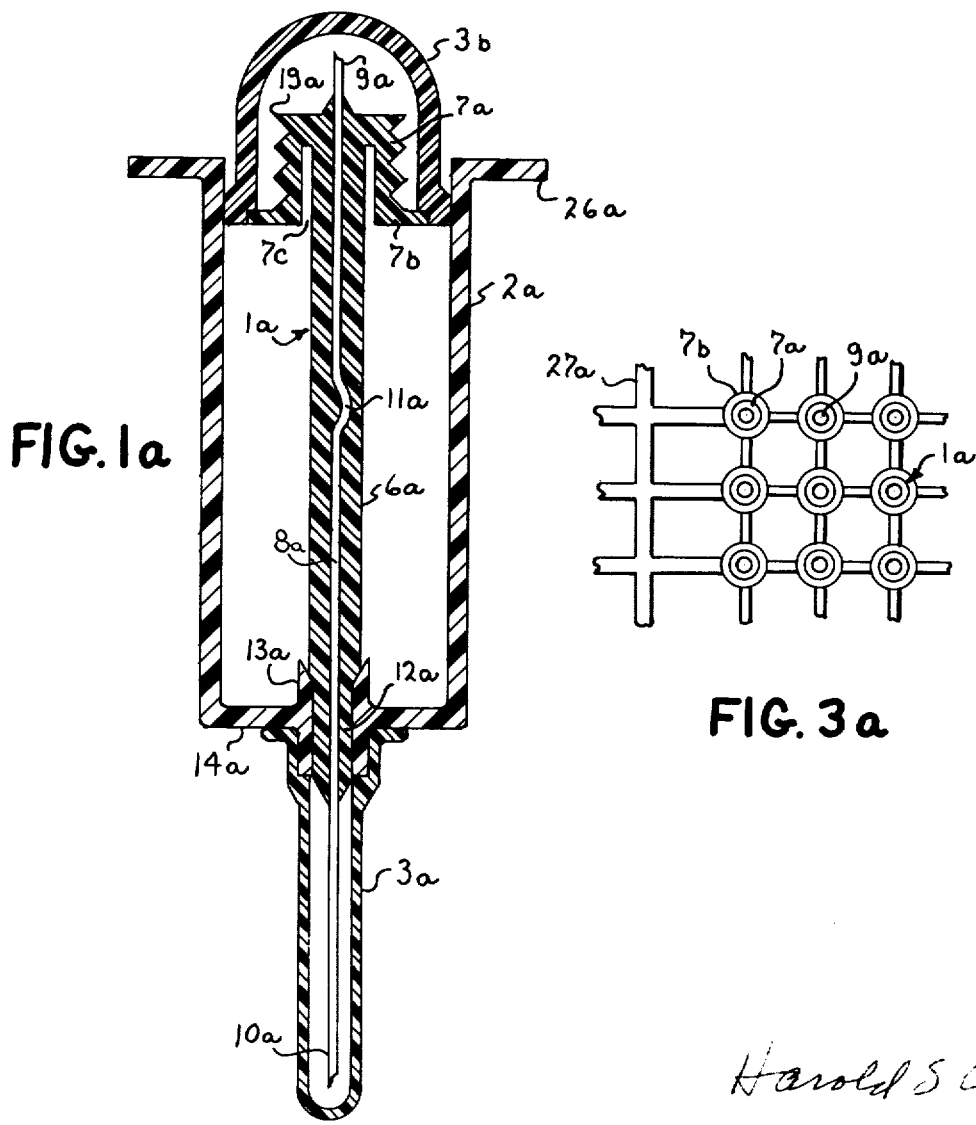
Figure 3A:
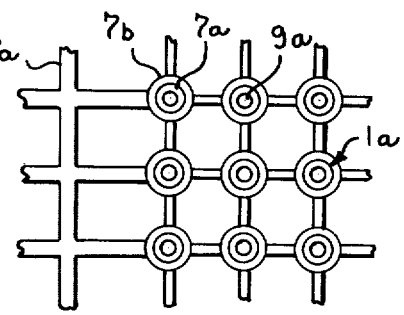
FIG. 3a, is a top plan view of a portion of a portion of a tree of molded plastic bodies.

The syringe of FIGS. 1a, 2a and 3a consists generally of a body 1a carrying the needle, a holder 2a enclosing the body, needle protectors 3a and 3b for the upper and lower ends on the needle, and a vial 4a filled with the desired dosage and closed by a stopper or piston 5a slidably received in the bore of the vial. In use, the open end of the vial is telescoped into the cylindrical wall of the holder, or over the body of the syringe and the stopper serves as a piston to expel the contents through the lower end of the needle. The vial is guided by the cylindrical wall of the holder for rotation and axial movement relative to the holder.

The body of the syringe is injection molded plastic and comprises a solid center post or hub 6a with a male coupling element 7a at its upper end of larger outside diameter than the hub. At the lower end of the part 7a is an integral flange 7b providing a mounting or sealing surface for the needle cap 3b. A reentrant recess 7c extends upwardly into the coupling part 7a around the hub. A double ended needle 8a is molded into the hub and has its pointed upper end 9a projecting above the coupling part 7a and has its pointed lower end 10a projecting out the lower end of the hub so as to be accessible for injection. The hub 6a has a length substantially equal to the maximum length of the vial to be used with the syringe so that the vial can be substantially completely telescoped over the hub.

In order to anchor the needle securely in the hub, the mid-section of the needle is provided with a bend 11a out of line with the ends 9a, 10a of the needle and opposite the cylindrical wall of the holder.

The lower end of the hub or post 6a has a reduced diameter section 12a telescoped within a hub 13a extending through the bottom wall 14a of the holder 2a. The holder 2a is a separately molded piece which is cemented or otherwise sealed or bonded to the reduced section 12a of the hub 6a. The needle protectors 3a and 3b are separately molded. The syringe comprises four separately molded plastic parts which are very easily injection molded and assembled together. The coupling part 7a has external threads 19a complementary to internal threads 20a on the female coupling element 21a integral with the stopper 5a.

When the syringe is to be used, the needle cap 3b covering the upper end 9a of the needle is removed and the coupling parts 7a and 21a are telescoped together while rotating the vial relative to the holder. This causes complete engagement of the threads 19a and 20a and forces the pointed end 9a of the needle through a web 23a closing the upper end of the stopper 5a, establishing communication between the liquid contents of the vial and the needle and also establishing a push or pull force resisting connection between the parts for transmitting axial forces in opposite directions. When the threads 19, 20 are fully engaged, continued rotation of the vial relative to the holder results in slippage between the stopper and vial. As the vial is pressed downward relative to the holder, the stopper acts as a piston forcing the liquid contents out through the needle 8a. The stopper 5a has external annular sealing ribs 25a which maintain the seal between the stopper and the inner side walls of the vial while permitting the necessary sliding movement. The holder 2a has a projecting flange 26a by which the holder may be gripped during injection.

The body 1a of the syringe is preferably molded in a multicavity mold in which plastic is injected through a plurality of interconnected runners 27a which feed the plastic into a plurality of locations around the coupling parts 7a. At the end of the molding cycle there is ejected from the mold a tree consisting of a plurality of bodies 1a connected to each other through a tree of runners 27a. The tree of molded parts can easily be handled as a unit. All of the molded parts will depend from the tree and will be in accurate relation to each other. In order to complete the assembly of the syringes, a plurality of needle protectors 3a and holders 2a are assembled into a fixture in which the holders and needle protectors are held on the same spacing as the bodies 1a in the tree 27a. The reduced sections 12a at the lower ends of the needle hubs 6a are coated with a suitable adhesive or solvent and the tree is then lowered so that each of the bodies 1 enters its holder. The solvent provides an adhesive coating. As the reduced sections 12a are telescoped within the hubs 13a of the holders, the parts are adhesively joined in assembled relation. At the end of the assembly, each body is joined or bonded to its holder and each needle is protected by its needle protector. In lieu of the adhesive or solvent, ultrasonic sealing may be used to bond the parts. In this process, ultrasonic vibrations cause local fusion of the plastic surfaces in contact with each other. After the joint has set up, the tree is broken to separate the individual syringes. After appropriate sterilization, each individual syringe is ready for use in conjunction with an appropriate vial as described above.

The body 1a, the holder 2a, and the needle holders 3a, 3b are made in simple molds. The body and holder are easily assembled. The needle protectors 3a, 3b maintain the needle in sterile condition. The coupling parts 7a, 21a are examples of the class of telescoping couplings which when engaged establish a push or pull connection so that after engagement, the plunger may be pulled outward to aspirate blood from a vein into the needle to determine that a vein has been punctured.

What is claimed is:
1. In combination,
 1. a cylindrical vial having a closed end and an open end sealed by a resilient stopper in slidable sealing engagement with the bore of the vial,
 2. a hollow needle open at both ends,
 3. an injection molded plastic body having a solid needle hub molded around a major portion of the length of the needle,
 4. means for anchoring the needle in the hub,
 5. one end of the needle being accessible for injection at one end of the needle hub and the other end of the needle being presented to the stopper at the other end of the needle hub,
 6. a coupling element integral with the stopper,

7. another coupling element integral with said other end of the needle hub.
8. said coupling elements having means interengaging by relative rotation and axial movement of said elements to establish a push or pull force transmitting connection between the stopper and the needle hub, said other end of the needle penetrating the stopper and communicating with the interior of the vial as the vial is moved axially relative to the needle hub to bring the coupling elements together so thereafter the contents of the vial may be injected by pressure on the closed end of the vial,
9. said plastic body, needle hub and other coupling element as molded having a runner leading to the coupling element and said plastic body, needle hub, other coupling element and runner as molded constituting a single piece of plastic,
10. the orthographic projection of said other coupling element on a plane at right angles to the axis of the needle hub being of larger outside diameter than the orthographic projection of said needle hub on said plane,
11. constructed so the needle hub, needle and said other coupling element may be injection molded and ejected as a unit from a simple mold with a runner leading to the coupling element,
12. and holding means interengaged with the vial and having a hub in telescoping relation with and fixed to the lower end of the needle hub and rotatably and slidably receiving and guiding the vial for holding the syringe while rotating the vial relative to the needle hub and to the holding means to engage the coupling elements and while exerting pressure on the closed end of the vial.

2. The unit of claim 1 in which the holding means has cylindrical walls guiding the vial for rotation and axial movement relative to the holder.

3. The unit of claim 1 in which the holding means is a separate cylindrical plastic holder, said separate cylindrical plastic holder having a bore rotatably and slidably receiving and guiding the vial.

4. The unit of claim 3 in which the bore in the cylindrical holder is closed around its hub.

* * * * *